(12) United States Patent
Oishi et al.

(10) Patent No.: US 8,771,174 B2
(45) Date of Patent: Jul. 8, 2014

(54) ENDOSCOPE-EQUIPPED PUNCTURE BALLOON

(75) Inventors: Hideto Oishi, Tokyo (JP); Yukihiko Sakaguchi, Akita (JP)

(73) Assignees: Sumitomo Bakelite Co., Ltd., Tokyo (JP); Hideto Oishi, Tokyo (JP)

( * ) Notice: Subject to any disclaimer, the term of this patent is extended or adjusted under 35 U.S.C. 154(b) by 1481 days.

(21) Appl. No.: 10/544,013

(22) PCT Filed: Jan. 30, 2004

(86) PCT No.: PCT/JP2004/000938
§ 371 (c)(1),
(2), (4) Date: Jan. 13, 2006

(87) PCT Pub. No.: WO2004/067080
PCT Pub. Date: Aug. 12, 2004

(65) Prior Publication Data
US 2006/0241345 A1    Oct. 26, 2006

(30) Foreign Application Priority Data

Jan. 30, 2003    (JP) .................................. 2003-022050
Mar. 13, 2003    (JP) .................................. 2003-068551

(51) Int. Cl.
*A61B 1/00*    (2006.01)
(52) U.S. Cl.
USPC ......... 600/116; 600/115; 600/127; 604/96.01
(58) Field of Classification Search
USPC ................ 600/104, 106, 114–116, 170, 173,
600/121–125; 604/28, 96, 95.01,
604/96.01–103.03; 606/194
See application file for complete search history.

(56) References Cited

U.S. PATENT DOCUMENTS

| | | | |
|---|---|---|---|
| 4,040,413 A * | 8/1977 | Ohshiro | 600/116 |
| 4,217,045 A * | 8/1980 | Ziskind | 396/17 |
| 4,384,584 A | 5/1983 | Chen | |
| 4,464,175 A * | 8/1984 | Altman et al. | 604/99.01 |
| 5,702,417 A | 12/1997 | Hermann | |

(Continued)

FOREIGN PATENT DOCUMENTS

| EP | 980691 A1 | 2/2000 |
|---|---|---|
| JP | 62-22623 | 1/1987 |

(Continued)

*Primary Examiner* — Matthew J Kasztejna
*Assistant Examiner* — Ryan Henderson
(74) *Attorney, Agent, or Firm* — Westerman, Hattori, Daniels & Adrian, LLP

(57) ABSTRACT

To provide a tool for safely and reliably securing a route for endermically approaching the interior of the body; more specifically, an endoscope-equipped puncture balloon that is designed to allow a balloon that does not immediately burst when punctured by a puncturing needle or the like to be used as a target, and that can be used by installing or inserting an endoscope in a tube holding such balloon.

In a thin-walled main body tube 1 equipped with an endoscope-installed section at the rear end, a balloon 2 is disposed on the front surface thereof, and a branch tube 4 communicating with the interior of the balloon 2 in a gas-liquid flow manner is disposed on the main body tube 1, the branch tube 4 having a connector 5 annexed to the rear end thereof; thus it is not until the liquid in the balloon is absorbed without the balloon immediately bursting when punctured by a puncturing needle that a bore can be secured until the balloon is contracted.

5 Claims, 12 Drawing Sheets

(56) References Cited

U.S. PATENT DOCUMENTS

| | | | |
|---|---|---|---|
| 6,007,482 A * | 12/1999 | Madni et al. | 600/115 |
| 6,059,719 A * | 5/2000 | Yamamoto et al. | 600/127 |
| 6,258,024 B1 * | 7/2001 | van Der Weegen | 600/115 |
| 6,306,081 B1 * | 10/2001 | Ishikawa et al. | 600/127 |
| 6,461,294 B1 * | 10/2002 | Oneda et al. | 600/116 |
| 2001/0056273 A1 * | 12/2001 | Ewers | 604/509 |
| 2002/0032457 A1 * | 3/2002 | Sirhan et al. | 606/195 |
| 2002/0042555 A1 * | 4/2002 | Komachi et al. | 600/115 |
| 2002/0103473 A1 * | 8/2002 | Roychowdhury et al. | 604/525 |
| 2003/0088154 A1 * | 5/2003 | Ishibiki et al. | 600/127 |
| 2004/0073088 A1 * | 4/2004 | Friedman et al. | 600/114 |

FOREIGN PATENT DOCUMENTS

| | | | |
|---|---|---|---|
| JP | 4-83201 | 7/1992 | |
| WO | WO 9936120 A1 * | 7/1999 | A61M 25/00 |
| WO | WO 02094087 A1 * | 11/2002 | A61B 1/267 |

* cited by examiner

ENDOSCOPE-EQUIPPED PUNCTURE BALLOON

TECHNICAL FIELD

The present invention relates to a tool for safely and reliably securing a route for endermically approaching the interior of the body, and more specifically, to a puncture balloon that is designed to allow a balloon that does not immediately burst when punctured by a puncturing needle or the like to be used as a target, and that can be used by installing or inserting an endoscope in a tube holding such balloon.

BACKGROUND ART

Heretofore, percutaneous endoscopic gastrostomy (PEG) as one of endoscopic operations for forming a fistula in the lumen of the stomach and on the skin surface of the abdominal wall using an endoscope was developed as a method of, in particular, enteral nutrition by Gaudert, a kid surgeon and Ponsky, an endoscopic sergeon in 1979 (refer to, for example, patent document 1), and further several procedures making use of it have been developed and are becoming widespread respectively. However, since the stomach wall and the abdominal wall are punctured, PEG cannot be used in "cases with a large amount of ascitic retention", "cases in which the liver and the transverse colon are present between the stomach and the adnominal wall", "cases with a past history of stomach surgery", and the like.

Further, although there is also a method of nasogastically indwelling a tube in the stomach, when it is indwelled therein for a long period, pain is strongly felt by the nasal passages, the nasal cavities, and the pharynx, and an ulcer is formed in the nasal passages, which makes it difficult to continuously indwell the tube. Further, there is even a case in which pneumonia is superinduced because it is difficult to eliminate sputum. PEG is also not preferable from the view point of these QOLs.

Further, Nakano et al developed a method of forming a cervical esophagus fistula under the X-ray clairvoyance in 1993. An indwelling method is such that a tube with a balloon is nasogastrically inserted in the esophagus, barium meal is injected into the balloon in the cervical esophagus, and the lumen of the cervical esophagus is expanded. Then, the cervical esophagus is endermically punctured under the X-ray clairvoyance to thereby form a cervical esophagus fistula, and a nutrition tube is indwelled therein. The indwelling method is simple, a patient is less invaded and pained, and the forming method is effective to a long-term nutrition management. However, since puncturing is executed only under the X-ray clairvoyance, there is a possibility of danger from the view point of the anatomical structure of the neck. Further, since the tube with the balloon uses a Foley catheter, whether or not a puncturing needle reaches the lumen of the esophagus when punctured is determined by that the balloon bursts. Thus, a worry arises in that the wall of the esophagus may be damaged by the extreme end of the needle after the balloon bursts and that since the puncturing needle is punctured shallow, it may be removed from the wall of the esophagus.

In contrast, Ohishi et al, who are the inventors of the present invention, improved the method of forming the cervical esophagus fistula under the X-ray clairvoyance of Nakano et al and devised a method of safely and reliably puncturing the balloon of a balloon catheter by a puncturing needle while confirming the position of the balloon from the outside of the body using an ultrasonic probe (refer to, for example, non-patent documents 1 and 2). However, this method also employs a Foley catheter likewise Nakano et al and still has a worry in that the wall of the esophagus may be damaged by the extreme end of a puncturing needle after the balloon bursts and that the needle may be removed from the wall of the esophagus.

To cope with the problem, the inventors of the present invention further improved the method of forming the cervical esophagus fistula and intended to form the cervical esophagus fistula at a bedside by composing the balloon of a balloon catheter to be punctured of a balloon which does not burst even it is punctured and combining the balloon with a dedicated introduction tool (refer to, for example, patent document 2) without using an X-ray apparatus and an endoscope. However, it could not be perfectly omitted to use the X-ray apparatus in minute manipulations such as a manipulation for eliminating a guide wire from the balloon catheter, and the like.

[Patent document] Japanese National-Publication-of-translated-version No. 6-503243
[Patent document 2] Pamphlet of International Publication No. 99/36120
[Non-patent document 1] Ohishi "Percutaneous endoscopic gastrostomy and its application and usefulness"
[Non-patent document 2] Ohishi "Percutaneous endoscopic gastrostomy and its knacks and related injuries"

DISCLOSURE OF THE INVENTION

An object of the present invention, which was made in view of the above circumstances, is to provide a tool for safely and reliably securing a route for endermically approaching the interior of the body, and more specifically, to provide an endoscope-equipped puncture balloon that is designed to allow a balloon that does not immediately burst when punctured by a puncturing needle or the like to be used as a target, and that can be used by installing or inserting an endoscope in a tube holding such balloon.

That is, a first invention is arranged as described below.

(1) In a thin-walled main body tube having an endoscope-installed section at a rear end, a balloon is disposed on the front surface thereof, a branch tube communicating with the interior of the balloon in a gas-liquid flow manner is disposed to the main body tube, and further a connector is annexed to the rear end thereof, wherein it is not until the liquid in the balloon is absorbed without the balloon immediately bursting when punctured by a puncturing needle that a bore can be secured until the balloon is contracted.

(2) The endoscope-equipped puncture balloon according to the description (1) is a balloon having a wall thickness of 0.01-1 mm, tensile strength of 8-25 MPa, 100% modulus of 3-6 MPa, elongation of 300-460%, and balloon inside pressure of 2.8-75 psi.

(3) The endoscope-equipped puncture balloon according to the description (1) or (2) is a balloon in which the main body tube has transparency for allowing the interior of the balloon to be visually recognized from the endoscope.

(4) The endoscope-equipped puncture balloon according to any of the descriptions (1)-(3) is a balloon in which the length from the extreme end of the main body tube or from the extreme end of the balloon to the extreme end of the endoscope-installed section is 50 mm or less.

(5) The endoscope-equipped puncture balloon according to any of the descriptions (1)-(4) is a balloon in which when the balloon is expanded, the balloon is disposed on the front side of the extreme end of the endoscope-installed section over the entire length in the lengthwise direction thereof.

(6) The endoscope-equipped puncture balloon according to any of the descriptions (1)-(5) is a balloon in which at least the balloon-installed section on the extreme end side of the balloon is disposed inside of the balloon with respect to the lengthwise direction of the balloon.

A second invention is arranged as described below.

(7) In an endoscope-equipped puncture balloon including a thin-walled inner cylinder having an endoscope-installed section formed to the rear end thereof, a thin-walled slide cylinder having a balloon disposed on the front surface of the extreme end thereof and fitted on the inner cylinder so as to move in the axial direction of an endoscope, and a branch tube communicating with the interior of the balloon in a gas-liquid flow manner and having a connector annexed to the rear end thereof, it is not until the liquid in the balloon is absorbed without the balloon immediately bursting when punctured by a puncturing needle that a bore can be secured until the balloon is contracted.

(8) The endoscope-equipped puncture balloon according to the description (7) is a balloon in which the balloon has a wall thickness of 0.01-1 mm, tensile strength of 8-25 MPa, 100% modulus of 3-6 MPa, elongation of 300-460%, and balloon inside pressure of 2.8-75 psi.

(9) The endoscope-equipped puncture balloon according to the description (7) or (8) is a balloon in which the inner tube and the slide cylinder have transparency for allowing the interior of the balloon to be visually recognized from the endoscope.

(10) The endoscope-equipped puncture balloon according to any of the descriptions (7)-(9) is a balloon in which when the slide cylinder is moved back to the movement end position thereof, both the length from the extreme end of the slide cylinder to the extreme end of the endoscope-installed section and the length from the extreme end of the inner cylinder to the extreme end of the endoscope-installed section are 10 mm or less, thereby when the slide cylinder is moved back to the movement end position, the slide cylinder does not interfere with the curved section of the endoscope.

(11) The endoscope-equipped puncture balloon according to any of the descriptions (7)-(11) is a balloon in which a stopper is disposed to one or both of the inner cylinder and the slide cylinder to prevent or suppress the backward movement of the slide cylinder when the slide cylinder is moved forth to the movement start position thereof with respect to the inner cylinder.

(12) The endoscope-equipped puncture balloon according to any of the descriptions (7)-(11) is a balloon in which at least the balloon-installed section on the extreme end side of the balloon is disposed inside of the balloon with respect to the lengthwise direction of the balloon.

Further, a third invention is arranged as described below.

(13) In an endoscope-equipped puncture balloon including a main body tube, which has a balloon disposed on the front surface of the extreme end thereof and includes an endoscope insertion lumen passing therethrough from the rear end to the front end thereof and a sub-lumen communicating with the interior of the balloon in a gas-liquid flow manner, the endoscope insertion lumen having an endoscope-inserted section at the rear end thereof, and the sub-lumen having a connector connected to the rear end thereof to expand and contract the balloon, it is not until the liquid in the balloon is absorbed without the balloon immediately bursting when punctured by a puncturing needle that a bore can be secured until the balloon is contracted.

(14) The endoscope-equipped puncture balloon according to the description (13) is a balloon in which the balloon has a wall thickness of 0.01-1 mm, tensile strength of 8-25 MPa, 100% modulus of 3-6 MPa, elongation of 300-460%, and balloon inside pressure of 2.8-75 psi.

(15) The endoscope-equipped puncture balloon according to the description 13 or 14 is a balloon in which the main body tube can visually recognize the interior of the balloon from the endoscope.

(16) The endoscope-equipped puncture balloon according to any of the descriptions (13)-(15) is a balloon in which at least the balloon-installed section on the extreme end side of the balloon is disposed inside of the balloon with respect to the lengthwise direction of the balloon.

(17) The endoscope-equipped puncture balloon according to any of the descriptions (3)-(16) is a balloon in which the endoscope insertion lumen has a film-like seal member having a slit or hole and annexed to the rear end thereof.

Endermic routes for various purposes can be made safely and reliably to all the duct cavities and the internal organs (esophagus, stomach, bile duct, pancreatic duct, bowel, urinary duct, bladder, and the like) using the puncture balloon of the present invention equipped with the endoscope.

BRIEF DESCRIPTION OF THE DRAWINGS

Next, the present invention will be specifically explained with reference to drawings.

BEST MODE FOR CARRYING OUT THE INVENTION

Figure 1:
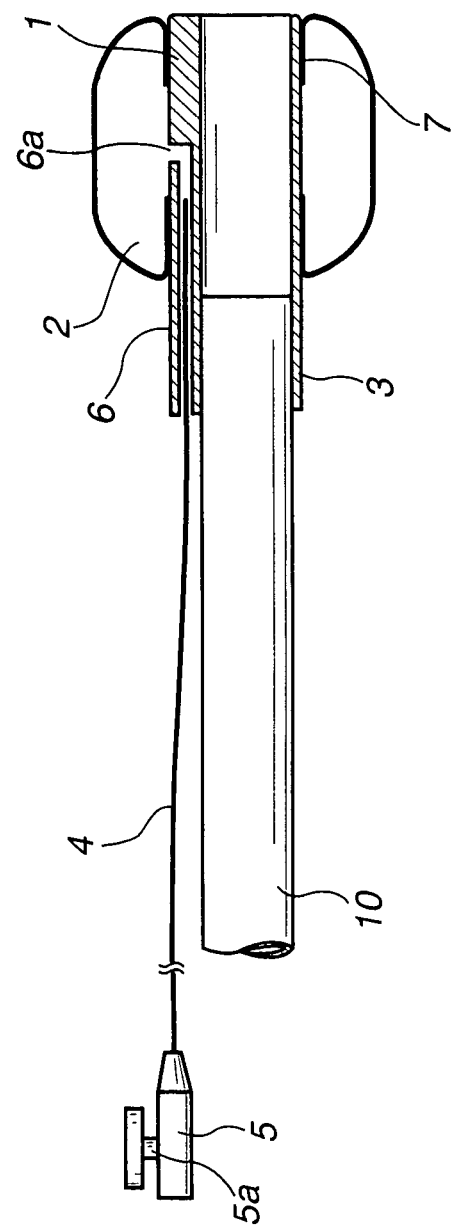
FIG. 1 is a side sectional view of an endoscope-equipped puncture balloon as a first embodiment of a first invention.

Firstly, an example of an endoscope-equipped puncture balloon for confirming a puncture position according to a first embodiment will be explained. As shown in FIG. 1, the puncture balloon of the first invention is composed of a main body tube 1, a balloon 2, an endoscope-installed section 3, a branch tube 4, and a connector 5.

The main body tube 1 of FIG. 1 is a thin-walled main body tube and has one or more lumens, and one of the lumens is a balloon expansion lumen 6 which has a closed extreme end and a side hole 6a that opens in the lumen of the balloon. Further, it is preferable that the main body tube 1 be formed in a diameter approximately the same as that of an endoscope 10 to be used according to the constitution of a patient and an insert position, it is preferable that the main body tube 1 have a projecting length of 50 mm or less from the extreme end of the endoscope so that the inserting property thereof is not deteriorated by that the length from angle section of the endoscope at the extreme end thereof is made too long, and it is more preferable that the main body tube 1 have the projecting length of 30 mm or less together with the length of the balloon. Further, the main body tube 1 has appropriate flexibility and elasticity due to ordinary room and body temperatures, and synthetic resin, for example, soft vinyl chloride resin, polyurethane resin, silicone rubber, or the like is ordinarily preferably used as a material for forming the main body tube 1. However, the material of the main body tube 1 is by no means limited thereto, and it is preferable that the material used to the main body tube 1 have such a degree of transparency as to allow the interior of the balloon to be visually recognized through the endoscope.

Figure 3:
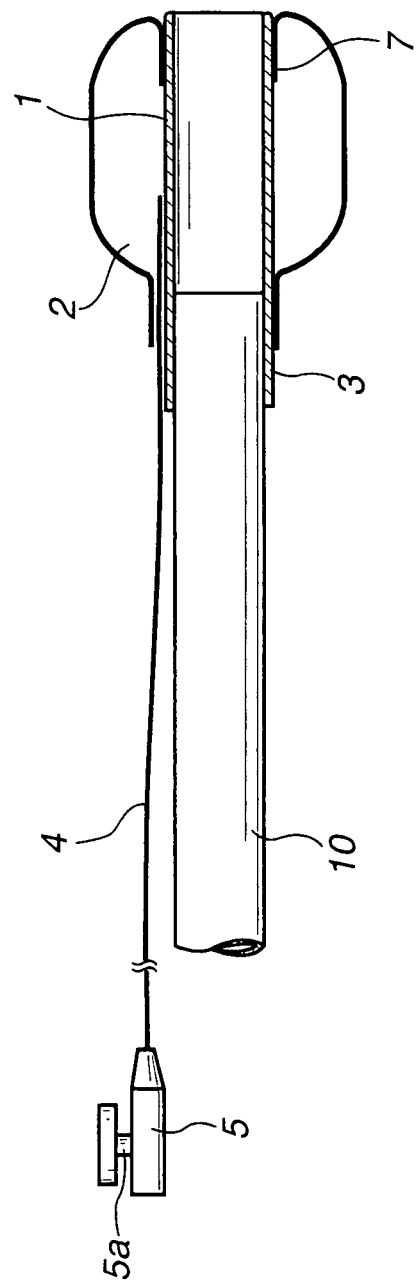
FIG. 3 is a side sectional view of an endoscope-equipped puncture balloon as another example of the first invention.

Note that, in the present invention, when the main body tube 1 is arranged to have a single lumen, the branch tube 4 to be described later may be directly disposed in the balloon 2 to be installed as shown in FIG. 3. It is preferable to install the branch tube 4 as exemplified in FIG. 3 because this is advantageous in that the main body tube 1 has improved flexibility, no directionality, and the like.

Figure 2:
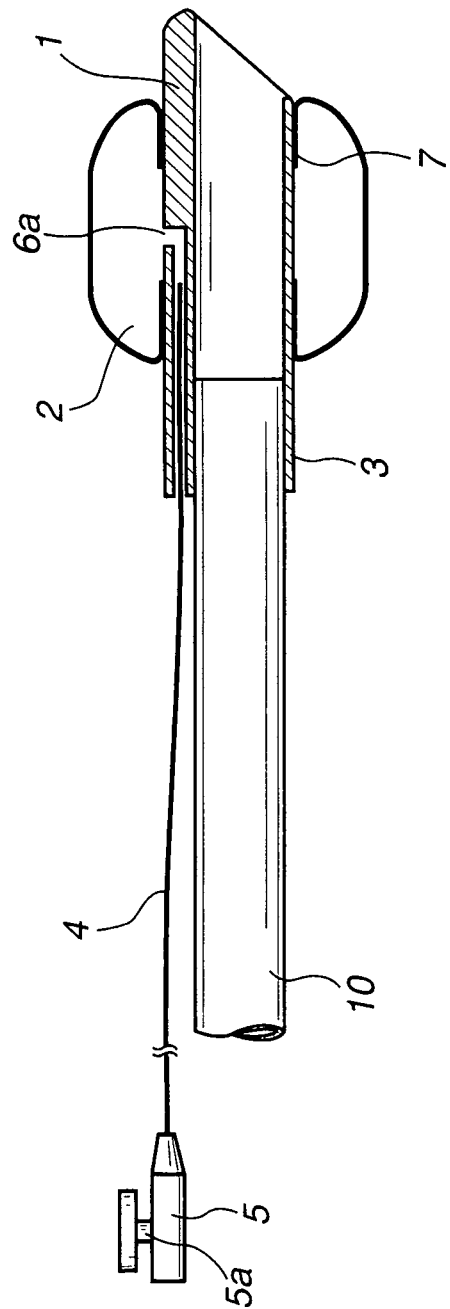
FIG. 2 is a side sectional view of the endoscope-equipped puncture balloon of FIG. 1 that uses another example as the main body tube thereof.

It is needless to say that the extreme end of the main body tube 1 is subjected to chamfering and the like to improve the insertion property thereof, and further it is preferable to cut the extreme end of the tube obliquely in place of cutting it at right angles to improve the insertion property thereof refer to FIG. 2.

The balloon 2 is formed to a length of 1-20 cm, an expanded diameter of 5-200 mm, and a wall thickness of 0.01-1 mm depending on a section into which it is inserted. When the balloon 2 is inserted, for example, nagosastrically, the wall thickness thereof is set to, for example, 0.1-0.3 mm to prevent it from being made bulky as much as possible. When the balloon 2 is used to the esophagus, the length thereof is approximately 3-10 cm, and the expanded diameter thereof is set to approximately 30 mm, and when the balloon 2 is used to the stomach, the length thereof is set to approximately 5-20 cm, and the expanded diameter thereof is set to approximately 200 mm.

Further, selected as a material for forming the balloon 2 is ordinarily synthetic resin having hardness of JIS SA 20-80°, tensile strength of 8-25 MPa, tearing strength of 20-60 kg/cm, 100% modulus of 3-6 MPa, elongation of 300-460%, and balloon inside pressure of 2.8-75 psi. Although soft vinyl chloride resin, polyurethane resin, silicone rubber, or the like, for example, are preferably used, the material is by no means limited thereto, and polyethylene, polyester, natural rubber latex, and the like may be used. Note that when the balloon 2 is formed using silicone rubber, natural rubber, or the like, there is a possibility that the balloon 2 immediately bursts due to the elasticity thereof when punched by a puncturing needle. Accordingly, the balloon 2 may be impregnated or laminated with nylon meshes and the like so that it does not immediately burst even if punctured by the puncturing needle.

As an example, when the balloon 2 to be orally inserted into the esophagus is formed of soft vinyl chloride resin, a material having hardness of approximately 60°, tensile strength of approximately 16 MPa, tear strength of approximately 45 kg/cm, 100% modulus of approximately 4.5 MPa, and elongation of approximately 400% is selected, and the wall thickness of the balloon is set to approximately 0.1-0.3 mm, and the outside diameter thereof is set to approximately ⅔ the desired expanded diameter thereof. With this arrangement, when a puncturing needle is stuck and its inner needle is pulled out the balloon 2 after it is expanded to the desired expanded diameter, the balloon 2 has such a suitable degree of internal pressure that a balloon expanding liquid is caused to flow out from a needle base by the internal pressure of the balloon. The balloon 2 is molded to a desired shape by blow molding, dip molding, extrusion molding, compression molding, and the like.

Further, as to a method of installing the balloon 2, it is desirable to minimize the projecting length thereof from the extreme end of the endoscope as described above, it is preferable that a balloon-installed section 7 on the extreme end side of the main body tube 1 be installed by being bent backward so that it is disposed inside of the balloon 2, and a means such as bonding, welding, or the like is selected to install the balloon 2.

The rear end of the main body tube 1 itself may be used as the endoscope-installed section 3 as long as the mounting/dismounting operationality of the rear end to the endoscope 10 can be satisfied by the material selected to the main body tube 1. However, it is also preferable to select different materials to the main body tube 1 and the endoscope-installed section 3, for example, to select soft vinyl chloride resin as the material of the main body tube 1 to prevent a puncturing needle from being passing therethrough and to select silicone rubber as the material of the endoscope-installed section 3 to secure flexibility in consideration of suitability of the materials to the respective components.

The branch tube 4 is used to couple the balloon 2 with the connector 5 to be described later in a gas-liquid flow manner and causes a liquid to flow to expand and contract the balloon 2. A material to be used to the branch tube 4 is not particularly limited as long as it has flexibility and sufficient strength, and soft vinyl chloride resin, polyurethane resin, silicone rubber, or the like are preferably used.

The connector 5 must be formed to have a lure taper so that it is connected to a syringe to inject a balloon expanding liquid and a liquid medicine. However, a valve member 5a (one-way valve, two-way turncock, three-way turncock, and the like) may be used, and further a connector having a lock type end may be used in some cases. Although the materials of the connector 5 and the valve member 5a are not particularly limited, synthetic resin such as soft vinyl chloride resin, polycarbonate resin, ABS resin, and the like may be preferably used.

Figure 4:
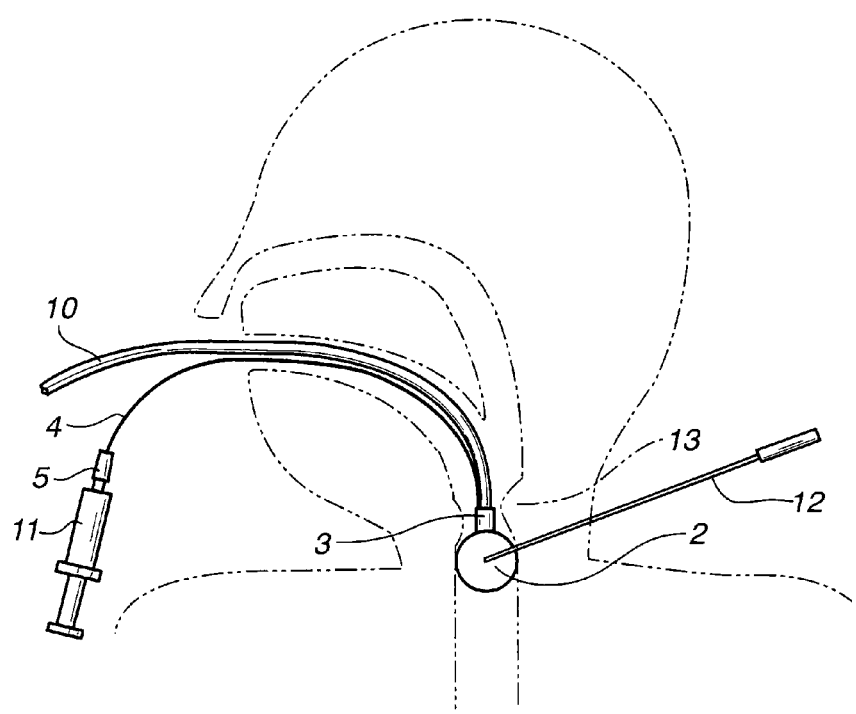
FIG. 4 is a schematic view showing an example of a method of using the puncture balloons of FIGS. 1 to 3.

Next, a method of endermically securing an insertion route from the cervical region to the esophagus will be explained as an example of a method of using the puncture balloon of the first invention explained with reference to FIGS. 1 and 2. As shown in FIG. 4, the puncture balloon 2 is orally inserted together with the endoscope-installed section 3 thereof installed to the extreme end of the endoscope 10 used to the upper digestive organ, the bronchial tube, and the other internal organs and tubes, the balloon 2 is expanded at a position beyond an esophagus inlet 13 by physiological saline or the like injected thereinto from the connector 5 to which the syringe 11 and the like is previously connected, further the endoscope 10 is pulled to secure a wide puncture region, and the position of the balloon 2 is confirmed by an ultrasonic probe applied to the cervical region from a body surface.

The ultrasonic probe is more strongly pressed against the body surface to secure a state in which the hyroid, the throat, the artery, the vein, and the like are offset from the balloon 2, and a puncturing needle 12 is punctured to the balloon 2. It is confirmed by an endoscope image and an ultrasonic image that the balloon 2 neither burst nor contracts at the moment at which the puncturing needle 12 is punctured and that the extreme end of the puncturing needle 12 is reliably located in the interior of the balloon 2.

Next, a necessary amount of a guide wire (not shown) is inserted from the tail end of the puncturing needle 12, and the puncturing needle 12 is extracted. The guide wire is eliminated from the interior of the puncture balloon 2 while being directed toward the stomach while pushing the endoscope 10 and the balloon 2 inward. Then, the physiological saline or the like in the balloon 2 is absorbed by the syringe 11, thereby the balloon 2 is contracted and the endoscope 10 is pulled so as to return to the upper region of the esophagus. Then, a dilator (not shown) with a sheath is inserted from the tail end of the guide wire while visually recognizing and conforming it also by the endoscope 10 to thereby enlarge the punctured region, and the route to the interior the esophagus is secured by extracting only the dilator. With this operation, a catheter can be appropriately inserted thereafter.

The region in which the puncture balloon of the present invention is used and the method of using the puncture balloon have been explained above by the method of forming the route for endermically approaching from the cervical region to the interior of the esophagus. In addition to the above method and the region, however, it is also possible to secure a safe and reliable a route for endermically approaching all the duct cavities and the internal organs (esophagus, stomach, bile duct, pancreatic duct, bowel, ureter, bladder, and the like) by appropriately changing and selecting the sizes and the materials of the endoscope 10, the puncture balloon 2, and the puncturing needle 12 as well as a the guide wire, the dilator, the sheath, and the like to be used.

Figure 5:
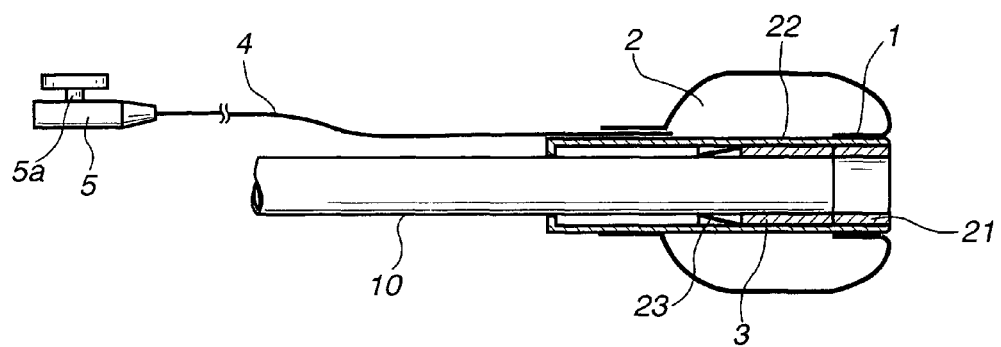
FIG. 5 is a side sectional view of an example of an endoscope-equipped puncture balloon as a first embodiment of a second invention in which a balloon is disposed at a retreat position.

Next, an endoscope-equipped puncture balloon for confirming a puncture position according to a second invention will be explained. As exemplified in FIGS. 5 and 6, the puncture balloon of the second invention is obtained by forming the main body tube 1 of the first invention to a two-piece type in which the main body tube 1 is composed of an inner cylinder 21 installed on the extreme end of an endoscope 10 and a slide cylinder 22 to which a balloon 2 is installed. In the exemplified example, the puncture balloon is composed of the inner cylinder 21 having an endoscope-installed section 3, the slide cylinder 22 having the balloon 2 on the surface thereof, a branch tube 4, and a connector 5.

The inner cylinder 21 is composed of a thin wall molded cylinder and formed to a diameter approximately the same as that of the endoscope 10 according to the constitution of a patient and an insert position. It is preferable that the inner cylinder 21 have a projecting length of 10 mm or less from the extreme end of the endoscope so that the inserting property thereof is not deteriorated by that the length thereof from the curved section of the endoscope at the extreme end thereof is increased. The endoscope-installed section 3, which is fitted on and fixed to the extreme end of the endoscope 10, is installed at the rear end of the inner cylinder 21 which is integrated with the endoscope-installed section 3 by a means such as bonding, welding, and the like.

The inner cylinder 21 having the endoscope-installed section 3 must be transparent and have a thin wall thickness, appropriate mechanical strength, and pinpoint dimensional accuracy so that the slide cylinder 22 to be described later can be fitted on the inner cylinder 21 so as to be free to slide on the inner cylinder 21 forward and backward without resistance (to cover the outside surface of the inner cylinder 21 in the form of a layer) and that the interior of the balloon can be visually recognized. Accordingly, it is preferable that the inner cylinder 21 be molded of resin that satisfies the above conditions. Materials to be used in these components are not particularly limited as long as they satisfy the above requirements, and, for example, polycarbonate resin, polyvinyl chloride resin, acrylic resin, ABS resin, polymethylpentene resin, polyamide resin, polyurethane resin, polyester resin, and the polymer alloys thereof are preferably used.

The endoscope-installed section 3 integrated with the inner cylinder 21 is preferably molded of a material having appropriate flexibility so that it is unlike to separate from the endoscope 10 and does not damage the endoscope 10 by being engaged therewith too tightly on the contrary. The material is not particularly limited as long as it satisfies the conditions, and, for example, thermoplastic elastomer and various kinds of rubber are particularly preferably used.

The slide cylinder 22 is composed of a thin wall molded cylinder and fitted on the inner cylinder 21 so as to be free to slide thereon forward and backward without resistance, and the balloon 2 is disposed on the surface thereof. When the slide cylinder 22 is moved back to the movement end position thereof, the extreme end position of the slide cylinder 22 is located at the position approximately the same position as the extreme end of the inner cylinder 21 (refer to FIG. 5) so that the inserting property of the endoscope is not deteriorated when it is inserted, and it is important that the rear end position of the slide cylinder 22 at the time have a length that does not interfere with the adjustment of the curving of the extreme end of the endoscope.

Figure 6:
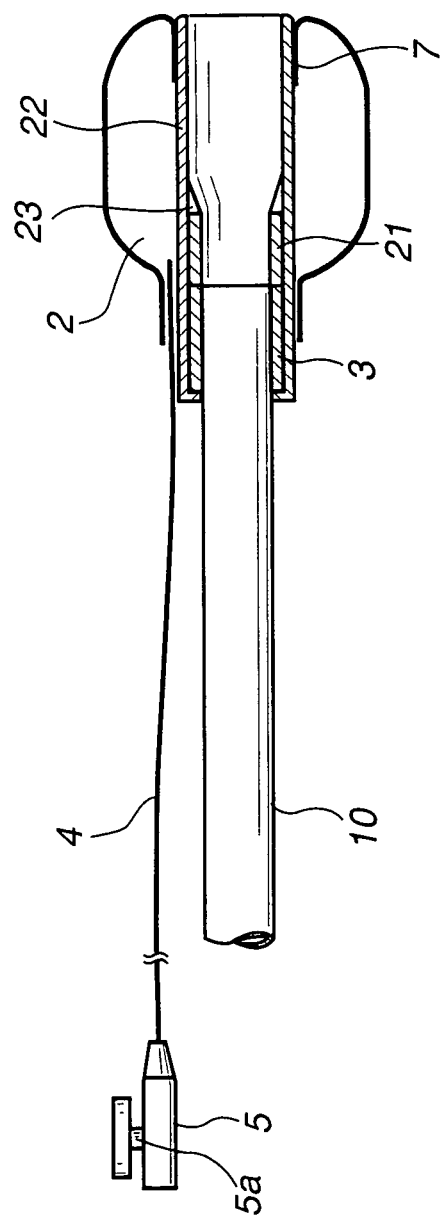
FIG. 6 is a side sectional view of the endoscope-equipped puncture balloon of FIG. 5.

A stopper 23 is disposed to the lumen of the slide cylinder 22 to prevent the slide cylinder 22 from moving backward when it is moved forward to the initial moving end thereof (refer to FIG. 6). The shape of the stopper 23 is not particularly limited, and, for example, a projection may be disposed to the slide cylinder 22 to hook the extreme end of the inner cylinder 21, or a projection may be disposed to the inner cylinder 21 on the contrary, and a groove may be formed to the slide cylinder 22 so that it is engaged with the projection. Note that it is preferable to form the stopper 23 in a shape that minimizes sliding resistance between the inner cylinder 21 and the slide cylinder 22.

A material, which satisfies the same requirements as those of the main body tube 1 described above and is suitable to install the balloon 2 and the branch tube 4, is selected as the material of the slide cylinder 22, and, for example, polycarbonate resin, polyvinyl chloride resin, acrylic resin, ABS resin, polymethylpentene resin, polyamide resin, polyurethane resin, polyester resin, and the polymer alloys thereof are preferably selected.

The conditions of the balloon 2 in the puncture balloon of the second invention such as the shape, size, wall thickness thereof, the material thereof, and the method of molding it, the method of installing it to the endoscope are the same as those of the example of the first embodiment. Likewise, the branch tube 4 and the connector 5 are also the same as those of the example of the first invention.

Figure 7:
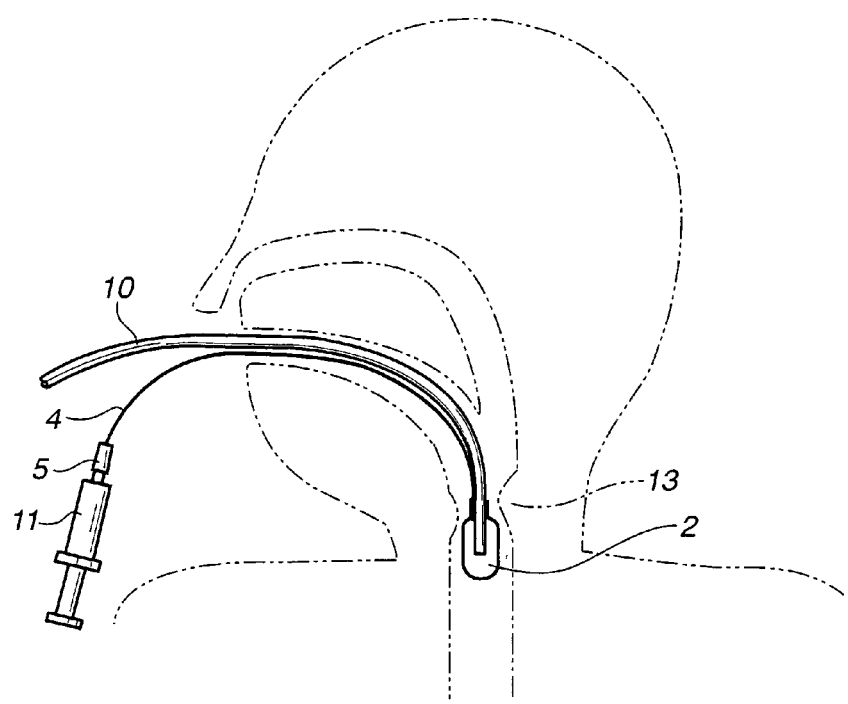
FIG. 7 is a schematic view showing an example in which the puncture balloon of the second invention exemplified in FIG. 6 is inserted into an esophagus inlet.
Figure 8:
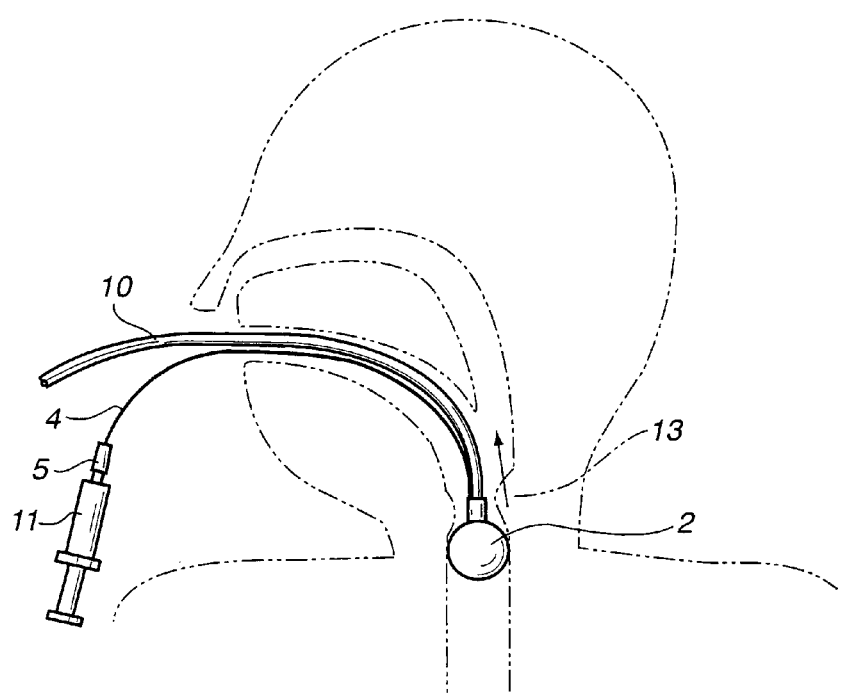
FIG. 8 is a schematic view showing a state in which an endoscope is pulled while expanding the puncture balloon inserted beyond the esophagus inlet in FIG. 7.
Figure 9:
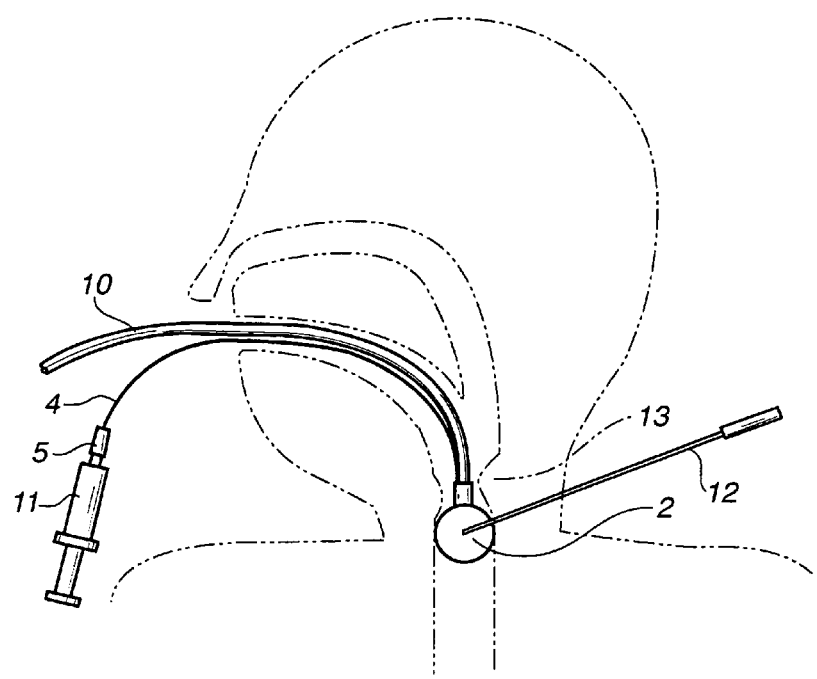
FIG. 9 is a schematic view showing a state in which a puncture needle is punctured into the puncture balloon of FIG. 8.

In the puncture balloon of the second invention, since the slide cylinder 22, to which the balloon 2 is installed, is slidably fitted on the inner cylinder 21 to which the extreme end of the endoscope 10 is installed, the slide cylinder 22 is designed such that the extreme end side thereof does not extend beyond the curved section of the endoscope at the position where the slide cylinder 22 is moved to the rearmost position thereof when the balloon 2 is inserted into the duct cavity and the internal organ. With this arrangement, the insertion property of the puncture balloon into the esophagus is not deteriorated, and when the balloon 2 is inserted beyond an esophagus inlet 13 (refer to FIG. 7), the endoscope 10 is pulled so that the positional relation between the balloon 2 and the extreme end of the endoscope 10 is changed to the positional relation shown in FIG. 6 so that a puncture operation can be visually recognized easily. This is to avoid the deterioration of insertion property into the esophagus caused by that the extreme end side of the slide cylinder 22 extends beyond the curved section of the endoscope 10 as well as to previously prevent such a problem as that when the extreme end of the endoscope is covered with the balloon and the slide cylinder, it is difficult to visually recognize the puncture operation and thus the endoscope is punctured and broken. Accordingly, in the puncture balloon of the second invention, when the balloon can be inserted to the predetermined regions of the cavity tube and the internal organ, the endoscope 10 is pulled and returned (refer to FIG. 8), thereby the puncture balloon can be punctured without causing any problem (refer to FIG. 9).

Figure 10:
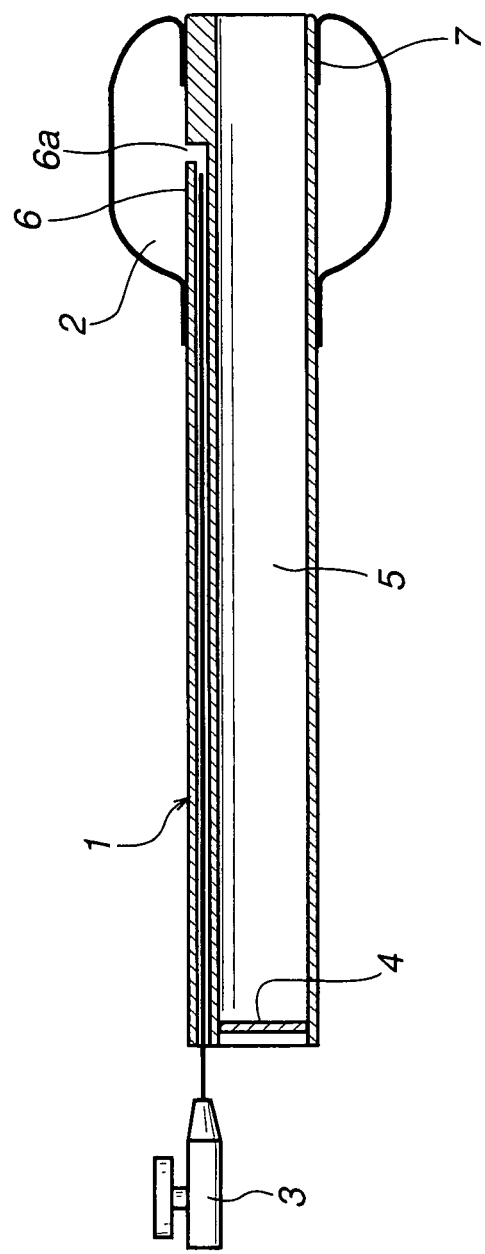
FIG. 10 is a side sectional view of a puncture balloon as a first embodiment of a third invention.
Figure 11:
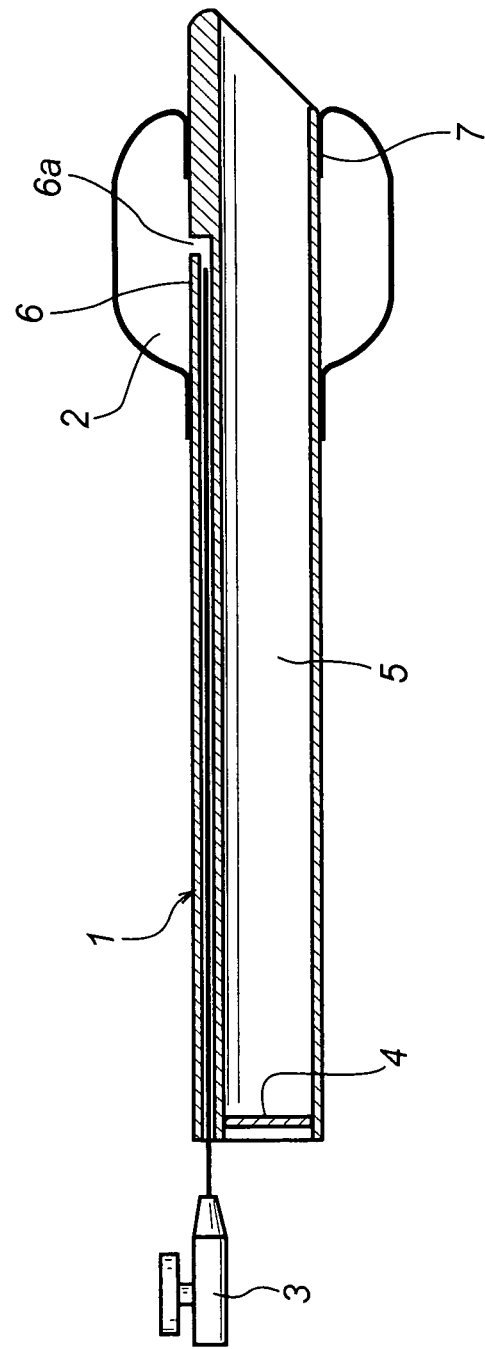
FIG. 11 is a side sectional view showing another example of an overtube of the puncture balloon of FIG. 10.
Figure 12:
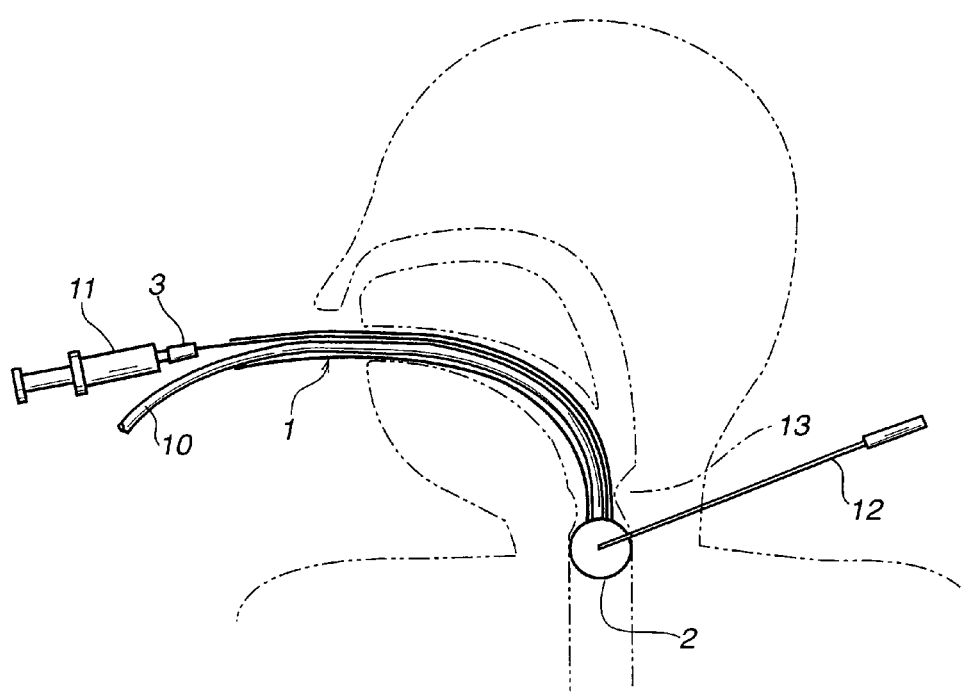
FIG. 12 is a schematic view explaining how the puncture balloon having the endoscope insertion overtube of FIG. 11 is used.

Subsequently, an example of a puncture balloon with an overtube for inserting an endoscope of a third invention will be explained refer to FIG. 10-FIG. 12. As exemplified in FIG. 10, the overtube of the puncture balloon of the third invention is composed of a main body tube 1, a balloon 2, and a connector 4. The main body tube 1 is composed of a thin wall tube and has an endoscope insertion lumen 5 and a sub-lumen 6. The endoscope insertion lumen 5 has such geometries including an inside diameter and the like and properties that an endoscope 10 can be inserted into and pulled out from the main body tube 1 passing therethrough from the extreme end to the rear end thereof. The sub-lumen 6 has a closed extreme end and a side hole 6a opened to the lumen of the balloon 2, and the rear end of the sub-lumen 6 communicates with the connector 4 and injects and evacuates a balloon expanding fluid into and from the lumen of the balloon 2. Note that the extreme end of the main body tube 1 is chamfered and cut obliquely likewise the embodiments described previously to improve the insertion property thereof.

It is preferable to reduce the outside diameter of the main body tube 1 as much as possible while securing the inside diameter thereof through which the endoscope to be used can be inserted, that is, to make the wall thickness thereof thin. However, an appropriate size is set to the main body tube 1 to prevent the lumen thereof from being closed when the tube 1 is bent. Accordingly, as one of preferable embodiments, the main body tube 1 is composed of a composite tube and provided with resin or metal meshes embedded therein. The length of the main body tube 1 is set in conformity with a target region. Further, the main body tube 1 has appropriate flexibility and elasticity due to ordinary room and body temperatures, and synthetic resin, for example, soft vinyl chloride resin, polyurethane resin, silicone rubber, or the like are ordinarily used preferably as a material for forming the main body tube 1. However, the material of the main body tube 1 is by no means limited thereto.

Further, it is preferable that the outer periphery or the lumen of the main body tube 1 of the present invention be subjected to lubrication processing, and, as examples of the processing, various kinds of hydrogel are practically coated, in addition to coating of fluorine resin and blending of silicone oil to the material thereof, and collagen, polyvinylpyrolidone, polyacrylamide, and the like are preferable as the hydrogel in view of toxicity to human body. Utilized as a method of fixing the hydrogel to the main body tube 1 are a method of coating the hydrogel, which is previously made to a solution, to a catheter and then crosslinking it through glutaraldehyde, a method of coating the monomer of the hydrogel and then crosslinking it using a polymerization initiator, a method of coating a hydrogel solution denatured by a photoreactive cross-linking agent to the main body tube 1 and fixing it by light rays irradiated thereto, and the like. Further, the main body tube 1 is preferably formed of a material having such a degree of transparency as to allow the interior of the balloon 2 to be visually recognized under an endoscope.

The specific examples of the length, expanded diameter, wall thickness, and the like of the balloon 2 are the same as those of the examples of the first and second inventions described previously. The molding material of the balloon 2 and the physical properties and the mechanical characteristics of the molded balloon 2 as well as the layered structure and the specific example of the specific mode of the balloon 2, the molding method of the balloon 2, and the method of installing the balloon 2 to the main body tube 1, and the like are the same as those of the previous examples. Further, the connector 3 to be used is also the same as that of the previous examples.

It should be noted that the main body tube 1 of the third invention has the endoscope insertion lumen 5 passing therethrough from the extreme end to the rear end thereof to insert and pull out the endoscope into and from the endoscope insertion lumen 5. However, a film-like seal section 4 provided with a slit or a hole may be disposed to the rear end of the endoscope insertion lumen 5 to secure a degree of negative pressure on the extreme end side of the endoscope insertion lumen 5 when the endoscope must be manipulated for suction and the like in treatment. The hole or the slit to be installed has a size set slightly smaller than that of the endoscope 10. Although synthetic resin, for example, soft vinyl chloride resin, polyurethane resin, silicone rubber, or the like is preferably used as the material of the seal section 4, the material is by no means limited thereto.

Industrial Applicability

The present invention is arranged as described above, endermic routes for various purposes can be made safely and reliably to all the duct cavities and the internal organs (esophagus, stomach, bile duct, pancreatic duct, bowel, urinary duct, bladder, and the like) using the puncture balloon of the present invention equipped with the endoscope. Further, a procedure, which must be conventionally executed by many persons in an operating room and the like because an X-ray apparatus is used, can be executed by two persons as well as by a bed by combining the endoscope with the ultrasonic probe.

The invention claimed is:

1. An endoscope-equipped puncture balloon, comprising:
an endoscope,
an inner cylinder including an endoscope-installed section formed on a proximal end of said inner cylinder, an extreme distal end of said endoscope being attached to an inner surface of said endoscope-installed section of said inner cylinder,
a slide cylinder, said slide cylinder being fitted on an outer surface of said inner cylinder and movable in the axial direction of the endoscope relative to said inner cylinder and said endoscope,
a balloon disposed on an outer surface of said slide cylinder on a distal surface of an extreme distal end of said slide cylinder,
a branch tube communicating with the interior of the balloon in a gas-liquid flow manner, and
a connector annexed to a proximal end of said branch tube, wherein the balloon is formed such that the balloon does not burst when punctured by a needle, wherein the balloon is formed such that after the balloon is punctured by the needle, a bore of the balloon is maintained until the liquid in the balloon is absorbed and the balloon contracts, wherein the balloon has a wall thickness of 0.01-1 mm, tensile strength of 8-25 MPa, 100% modulus of 3-6 MPa, elongation of 300-460%, and balloon inside pressure of 2.8-75 psi, and wherein said inner cylinder and said slide cylinder compose main body tube having a length of 50 mm or less.

2. An endoscope-equipped puncture balloon according to claim 1, wherein the inner tube and the slide cylinder are transparent.

3. An endoscope-equipped puncture balloon according to claim 1, wherein when the slide cylinder is moved to a maximum extension position, a distance from an extreme distal end of the slide cylinder to an extreme proximal end of the endoscope-installed section of said inner cylinder is 10 mm or less, and wherein a distance from an extreme distal end of the inner cylinder to the extreme proximal end of the endoscope-installed section of said inner cylinder is 10 mm or less.

4. An endoscope-equipped puncture balloon according to claim 1, wherein at least one of said inner cylinder and the slide cylinder includes a stopper to prevent or suppress the backward movement of the slide cylinder when the slide cylinder is in a minimum extension position.

5. An endoscope-equipped puncture balloon according to claim 1, wherein said slide cylinder includes a balloon-installed section, said balloon installed section being inside of a lengthwise direction of the balloon.

* * * * *